(12) United States Patent
Posnick

(10) Patent No.: US 7,862,566 B2
(45) Date of Patent: Jan. 4, 2011

(54) MIDFACE EXTERNAL DISTRACTION METHOD AND APPARATUS

(76) Inventor: Jeffrey C. Posnick, 5530 Wisconsin Ave., Suite 1250, Chevy Chase, MD (US) 20815

( * ) Notice: Subject to any disclaimer, the term of this patent is extended or adjusted under 35 U.S.C. 154(b) by 1083 days.

(21) Appl. No.: 11/332,233

(22) Filed: Jan. 17, 2006

(65) Prior Publication Data

US 2006/0184168 A1 Aug. 17, 2006

Related U.S. Application Data

(60) Provisional application No. 60/646,655, filed on Jan. 26, 2005.

(51) Int. Cl.
*A61B 17/00* (2006.01)
(52) U.S. Cl. .............................. 606/54; 606/90; 606/105
(58) Field of Classification Search .................... 606/54, 606/90, 105
See application file for complete search history.

(56) References Cited

U.S. PATENT DOCUMENTS

| 5,147,358 A | 9/1992 | Remmler |
| 6,589,250 B2* | 7/2003 | Schendel ..................... 606/105 |
| 7,011,642 B2* | 3/2006 | Greene et al. .................. 602/36 |

OTHER PUBLICATIONS

Jeffrey A. Fearon, M.D., Crouzon Syndrome: Treatment, Sep. 9, 2003.*
KLS Martin L.P., "Red II System, Common Questions Regarding Rigid External Distraction (RED)" (3 pages), KLS Martin website at http://www.klsmartinusa.com/red.di/red.html, Jul. 17, 2006.
KLS Martin, L.P., "Rigid External distration (Red II) System Instrumentation for Le Fort I" (2 pages), KLS Martin catalog.

* cited by examiner

*Primary Examiner*—Eduardo C Robert
*Assistant Examiner*—Ellen C. Hammond
(74) *Attorney, Agent, or Firm*—Steptoe & Johnson LLP

(57) ABSTRACT

A method and apparatus for midfacial and maxillofacial external distraction includes attaching one end of each curved temporal bar to a skull and the other end to a surgically isolated (osteotomized) portion of the patient's midface (maxilla, orbit(s) or zygoma(s)).

29 Claims, 3 Drawing Sheets

MIDFACE EXTERNAL DISTRACTION METHOD AND APPARATUS

RELATED APPLICATION

The application claims the benefit of U.S. Provisional Application No. 60/646,655, filed Jan. 26, 2005, which is herein incorporated by reference in its entirety.

TECHNICAL FIELD

The present invention relates to midfacial and maxillofacial reconstruction.

BACKGROUND

Distraction is an appropriate method of treatment for certain medical conditions affecting midfacial and cranio-maxillofacial structure, such as Crouzon syndrome, which is characterized by a sunken midface, as well as jaw deformities giving rise from cleft palate.

SUMMARY

In one aspect, a method for distracting a region of a facial skeleton includes attaching a curved temporal bar to a skull such that the posterior temporal end of the temporal bar is attached to the skull at substantially eye- and temple-level and the anterior maxillary end curves around in front of the facial skeleton at the level of a midfacial or maxillofacial region, and securing the anterior maxillary end of the temporal bar to a midface or cranio-maxillofacial region of the facial skeleton, thereby applying a force to the attached region sufficient to effect distraction.

In another aspect, a method for distracting a region of a facial skeleton includes attaching a first temporal end of a distractor to the skull, attaching a second temporal end of a distractor to the skull, and securing a central region of the distractor to a midface or cranio-maxillofacial region of the facial skeleton, thereby applying a force to the attached region sufficient to effect distraction. The second temporal end can be adjustably positioned relative to the first temporal end by altering a dimension of the central region.

In another aspect, a midface external distractor includes a first temporal end, a second temporal end, and a central region between the first temporal end and the second temporal end, the central region including two or more locations for securing the distractor to a midfacial or maxillofacial region. The second temporal end can be adjustably positioned relative to the first temporal end by altering a dimension of the central region. The first temporal end is a portion of a first curved temporal bar and can include a first anterior maxillary end and the second temporal end is a portion of a second curved temporal bar including a second anterior maxillary end. The central region can be formed from the first anterior maxillary end and the second anterior maxillary end.

Advantageously, the distractor is easy to apply and remove, is more like orthodontic headgear, is more comfortable for the patient, offers unobstructed visual fields, has fewer moving parts, is more secure to the skull base, and provides protection to the midface when compared to other apparatuses used for midface and cranio-maxillofacial distraction. It also allows for oral food and liquid to be introduced without obstruction. Other apparatuses can be uncomfortable and complicated, are typically secured to the patient's skull at points significantly above the patient's eye level where the skull is thick, and can include components that project in front of the patient's eyes which obscure the patient's vision and attract attention to the apparatus. Additionally, components projected in front of the patient's eyes and attached to the midface or cranio-maxillofacial region can cause an undesirable torque force on the points where the device is attached to the skull significantly above eye level because of the divergent planes of attachment on the skull. This device also allows for an intraoperative nasal tracheal intubation tube to be used without interfering with device placement.

The details of one or more embodiments are set forth in the accompanying drawings and the description below. Other features, objects, and advantages will be apparent from the description and drawings, and from the claims.

DETAILED DESCRIPTION

Figure 1:
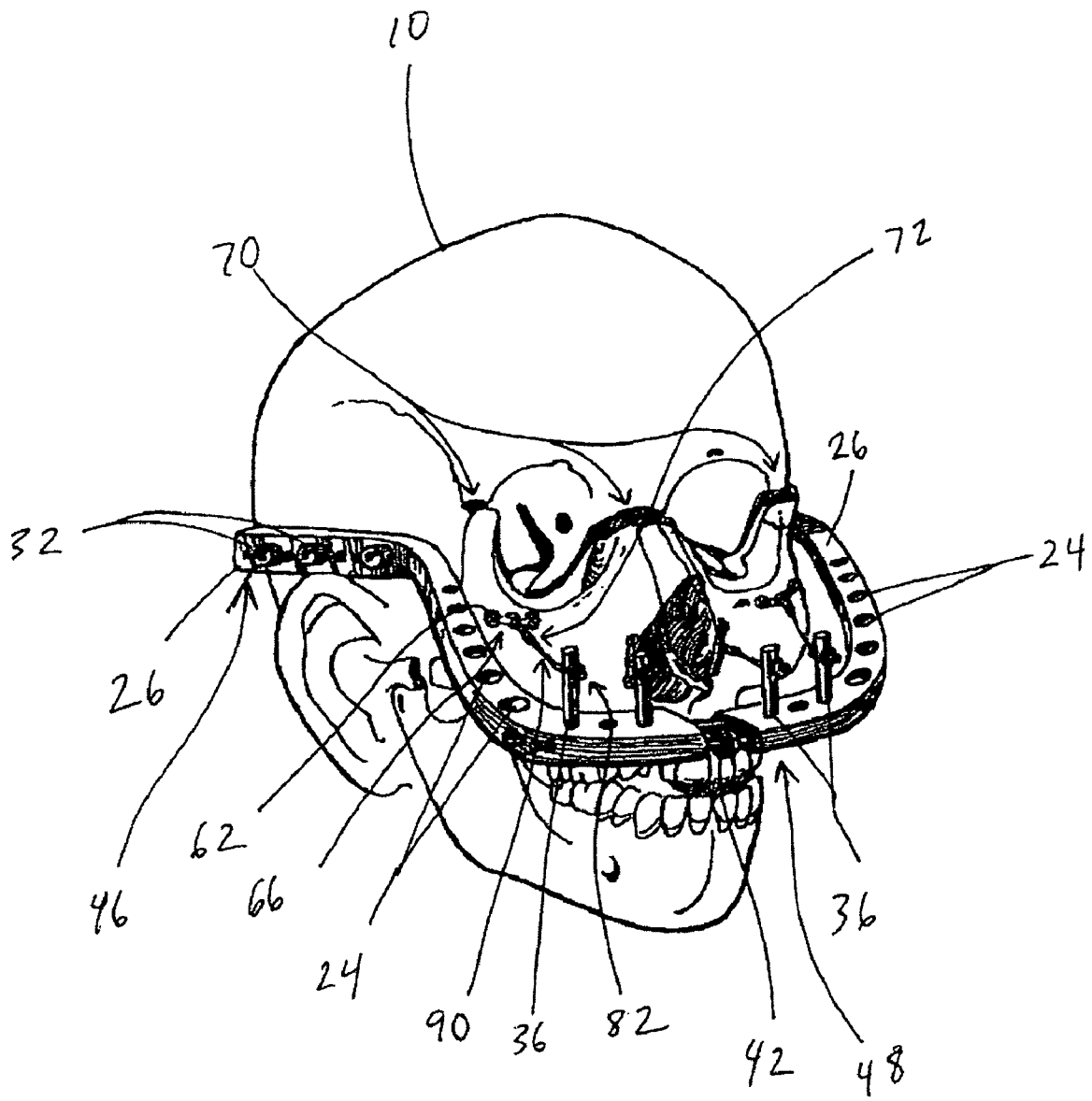
FIG. 1 is a drawing depicting an external distraction device functionally attached to a human skull in the midfacial region.

In general, a method and apparatus for midfacial and maxillofacial external distraction includes attaching one end of a curved temporal bar to a skull and the other end to a surgically isolated portion of the patient's midface or maxilla. Screws attached to the portion of the skull to be distracted are attached to screws which are themselves attached to a second end of the curved temporal bar. The screws attached to the portion of the skull to be distracted and screws attached to the curved temporal bar may be adjusted to effect distraction as desired. One temporal bar is attached to each side of the patient's skull, and the two temporal bars are joined near the patient's midface or cranio-maxillofacial region by a threaded rod, which provides further adjustment.

A method of midfacial or maxillofacial distraction can include anchoring a pair of half-U-shaped aluminum temporal bars to the patient's skull, with each half-U-shaped temporal bar anchored substantially at the level of the patient's eyes and temples. Each temporal bar as it extends from the anchor points at the back of the skull toward the patient's face includes a downward curve such that the temporal bar, as it begins to wrap around the patient's face extends below the patient's eyes to approximately the height of the midface or cranio-maxillofacial region desired to be distracted.

Each half-U-shaped temporal bar includes multiple threads for positioning and securing vertical rods screwed into the threads. The rods may be positioned in a manner appropriate to effect the desired midfacial or maxillofacial distraction. The rods are then attached to points in the midface or cranio-maxillofacial region for distraction. In the case of midfacial distraction, as with Crouzon syndrome patients, threaded fixation plates secured with screws into bone at the midfacial region include threaded fixation screws projecting outward from the face. Threaded distraction screws are secured into the vertical rods positioned in each half-U-shaped temporal bar. Heavy wires are provided between each threaded fixation screw and its corresponding distraction screw and as a result, adjustment to the fixation screws or distraction screws or the overall position of each half-U-shaped temporal bar on the skull provides a distraction force applied to the attached bone in the midfacial region including the zygoma, orbit, or maxilla. In dental applications, a pre-fabricated dental splint is attached to distraction screws with heavy wire in a manner that applies force that directs the affected maxillofacial region according to the desired reconstruction.

Each half-U-shaped temporal bar is attached to one side of the patient's skull. As the temporal bars extend toward the patient's face, the ends generally meet in front of the facial skeleton in the location to be affected in the midface or cranio-maxillofacial region desired to be affected. The two temporal bars are connected at their proximate ends by a threaded rod(s) which provides additional adjustment flexibility. By turning the threaded rod(s), the proximate ends of the temporal bars move together or apart, providing another adjustment option for the distraction force.

FIG. 1 shows an external distraction device functionally attached to a human skull. A posterior temporal end 46 of each half-U-shaped temporal bar 26 is attached on one side of the human skull 10 at a point substantially the same height at the level of the patient's eyes or temple. Temporal bar 26 is attached to human skull 10 with screws 32. As it extends forward toward the patient's face, temporal bar 26 slopes downward below the patient's eye level and around toward the front of the face to the height of the midface or cranio-maxillofacial region desired to be distracted. Temporal bar 26 includes a plurality of threads 24 into which vertical rods 36 are positioned according to a predetermined distraction plan. A distraction screw 82 is attached to each vertical rod 36.

Fixation plates 66 are attached to the facial bone at predetermined locations with screws 62. A fixation screw 72 is attached to each fixation plate, and each fixation screw 72 is connected to a corresponding distraction screw 82 by heavy wire 90. By adjusting the distraction screws 82 or fixation screws 72 a force is applied to the fixation plate 66 by the temporal bar 26 and attached vertical rod 36 such that the bone secured to fixation plate 66, having been surgically isolated (osteomized) at points 70 from the portion of skull 10 where temporal bar 26 is attached, may be repositioned according to a distraction plan.

Both temporal bars 26 meet at their anterior maxillary ends 48 and are preferably joined at anterior maxillary ends 48 by a threaded rod 42, which is preferably constructed from carbon, and which adds an additional element of adjustment to the external distraction apparatus.

Figure 2:
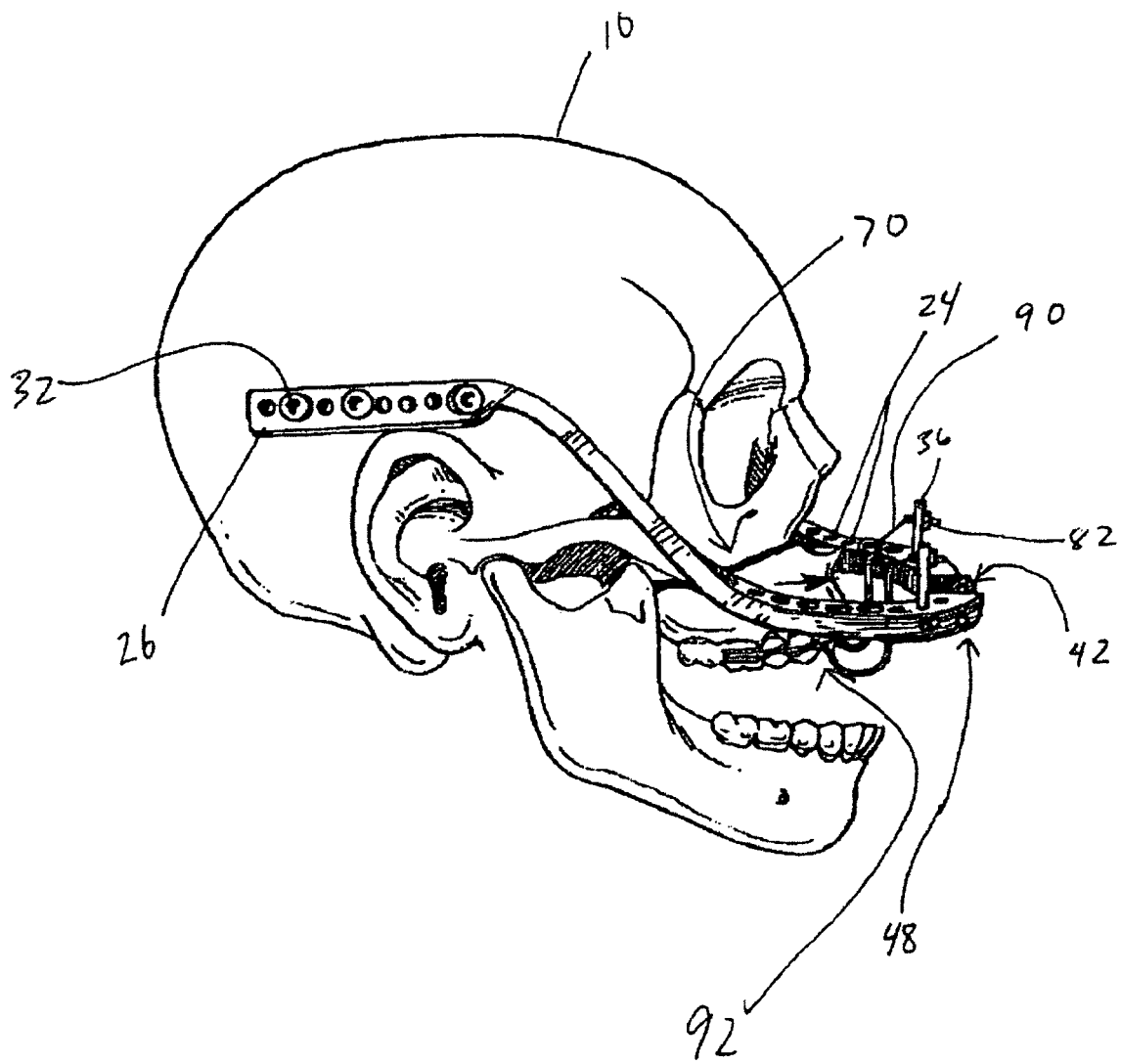
FIG. 2 is a drawing depicting a second view of an external distraction device functionally attached to a human skull in the maxillofacial region.

Referring to FIG. 2 a method and device are shown for distraction at a maxillofacial region as, for example, in treated a cleft palate patient with maxillary deformaty. A posterior temporal end 46 of each half-U-shaped temporal bar 26 is attached on one side of the human skull 10 at a point substantially the same height at the level of the patient's eyes or temple, as depicted in FIG. 1. Temporal bar 26 is attached to human skull 10 with screws 32. As it extends forward toward the patient's face, temporal bar 26 slopes downward below the patient's eye level and around toward the front of the face to the height of the midface or cranio-maxillofacial region desired to be distracted. Temporal bar 26 includes a plurality of threads 24 into which vertical rods 36 are positioned according to a predetermined distraction plan. A distraction screw 82 is attached to each vertical rod 36.

Dental splint 92 is secured to the maxilla, preferably by the patient's teeth. Dental splint 92 extends out of the patient's mouth and is attachable to distraction screw 82 by heavy wire 90. By adjusting the distraction screws 82 a force is applied to the dental splint 92 by the temporal bar 26 and attached to vertical rod 36 such that the maxilla secured to fixation plate 66, having been surgically isolated at points 70 from the portion of skull 10 where temporal bar 26 is attached, may be repositioned according to a distraction plan.

Both temporal bars 26 meet at their anterior maxillary ends 48 and are preferably joined at anterior maxillary ends 48 by a threaded rod(s) 42, which is preferably constructed from carbon (or another material), and which adds an additional element of adjustment to the external distraction apparatus.

Figure 3:
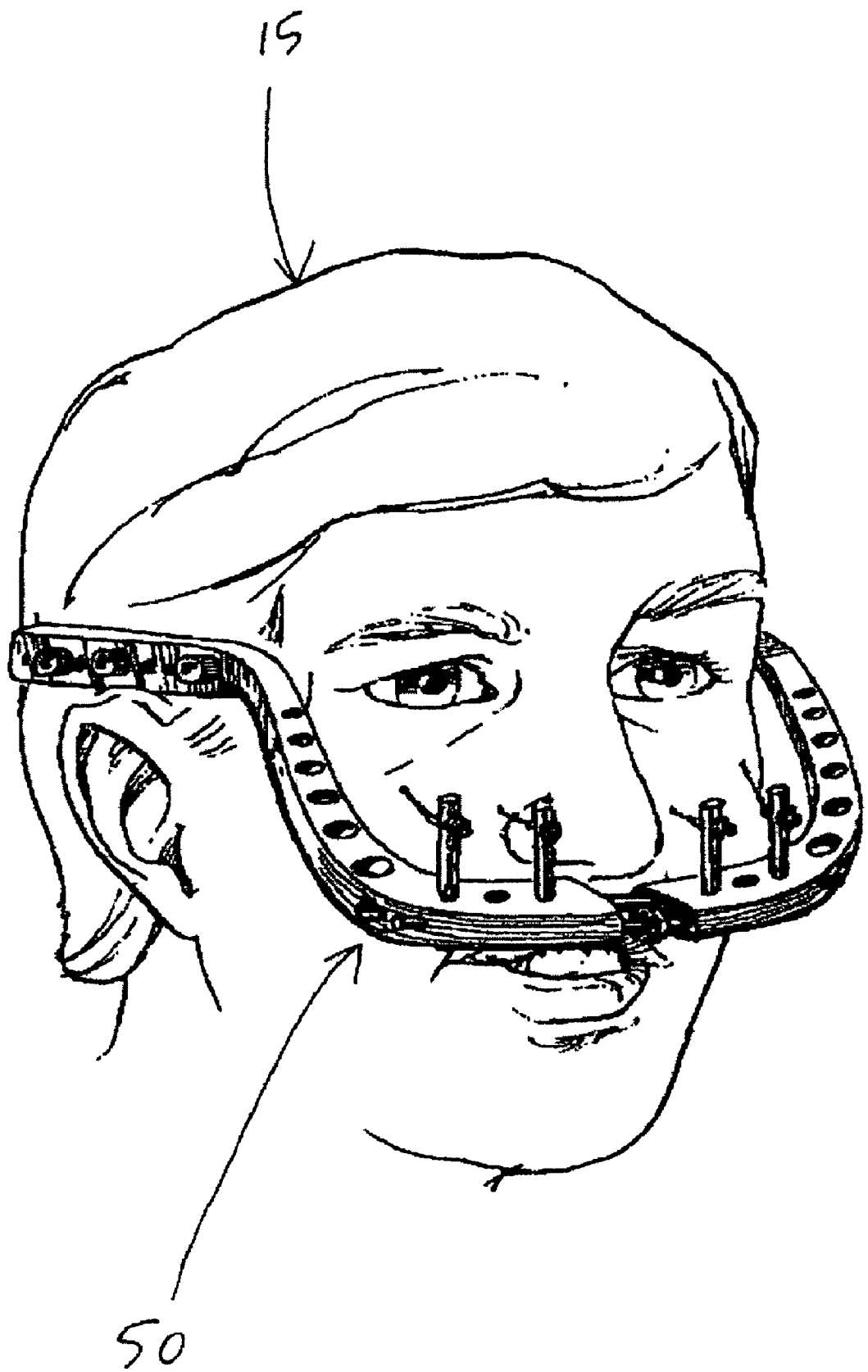
FIG. 3 is a drawing depicting a patient wearing an external distraction device functionally attached as depicted in FIG. 1.

Referring to FIG. 3, a human patient 15 is shown wearing the functionally attached external distraction apparatus 50. This view illustrates that the apparatus 50, even when attached to a midface region for distraction has an appearance similar to an orthodontic headgear device rather than a bulky and complicated halo-type skull headframe. The patient's vision is unobstructed, the oral cavity is unobstructed, and the curvature of the apparatus 50 provides a faceguard type-protection to the patient, and particularly to the region being distracted.

Other embodiments are within the scope of the following claims.

What is claimed is:

1. A method for distracting a region of a facial skeleton, comprising:
   attaching a curved temporal bar of a device to a skull such that the posterior temporal end of the temporal bar is attached to the skull at substantially eye- and temple-level, and the anterior maxillary end curves around in front of the facial skeleton at the level of a midfacial or maxillofacial region; and
   securing the anterior maxillary end of the temporal bar to a midface or cranio-maxillofacial region of the facial skeleton, thereby applying a force to the attached region sufficient to effect distraction.

2. The method of claim 1, wherein securing the anterior maxillary end of the temporal bar to a midface or cranio-maxillofacial region of the facial skeleton includes attaching to the midface or cranio-maxillofacial region of the facial skeleton a distraction screw adjustably secured to the anterior maxillary end of the device.

3. The method of claim 2, wherein the distraction screw is adjustably secured to a vertical rod and the vertical rod is secured to the anterior maxillary component of the device.

4. The method of claim 1, wherein the temporal bar is configured to provide a plurality of positions for securing the anterior maxillary component of the device to the midface or cranio-maxillofacial region of the facial skeleton.

5. The method of claim 4, wherein a threaded hole or attachment is located at each of the plurality of positions for securing the anterior maxillary end of the temporal bar to the midface or cranio-maxillofacial region of the facial skeleton.

6. The method of claim 1, wherein the temporal bar is configured to receive a vertical rod.

7. The method of claim 6, wherein the central anterior region includes a variable height attachment post.

8. The method of claim 1, wherein the temporal bar is configured to be attached to the skull with screws.

9. The method of claim 1, wherein the temporal bar extends from the posterior temporal end attached to the side of the skull and extends anterior to the front of the facial skeleton.

10. The method of claim 9, wherein the temporal bar includes an adjustable anterior maxillofacial component of the device.

11. The method of claim 1, wherein the temporal bar is configured to be adjustably paired with a second temporal bar, the second temporal bar configured to be attached to the side of the skull opposite the side to which the temporal bar is attached.

12. The method of claim 1, wherein the temporal bar is configured to be adjustably paired with a second temporal bar.

13. The method of claim 12, wherein the temporal bar is configured to be adjustably paired with a second temporal bar with at least a rod.

14. A method for distracting a region of a facial skeleton, comprising:
   attaching a first temporal end of a distractor to the skull at substantially eye- and temple-level;
   attaching a second temporal end of a distractor to the skull; and
   securing a central anterior region of the distractor to a midface or cranio-maxillofacial region of the facial skeleton, thereby applying a force to the adjacent region of the face sufficient to effect distraction,
   wherein the second temporal end is adjustably positioned relative to the first temporal end by altering a dimension of the central region.

15. The method of claim 14, wherein the distractor further comprises a first temporal bar including the first temporal end and a second temporal bar including the second temporal end.

16. The method of claim 15, wherein the first temporal bar and second temporal bar are curved.

17. The method of claim 15, wherein the first temporal bar and second temporal bar are configured to curve around in front of the facial skeleton at the level of a midface or cranio-maxillofacial region when the first temporal end is attached to the skull and the second temporal end is attached to the skull.

18. The method of claim 15, wherein the temporal bar is configured to receive a vertical rod.

19. The method of claim 18, wherein the central anterior region includes a variable height attachment post.

20. The method of claim 15, wherein the first temporal bar extends from the first temporal end attached to a first side of the skull to a first anterior maxillary end in front of the facial skeleton, and the second temporal bar extends from the second temporal end attached to a second side of the skull to a second anterior maxillary end in front of the facial skeleton.

21. The method of claim 20, wherein the first temporal bar and second temporal bar include an adjustable anterior maxillofacial component of the device.

22. The method of claim 15, wherein the first temporal bar and second temporal bar are configured to be adjustably paired.

23. The method of claim 22, wherein the first temporal bar and second temporal bar are configured to be adjustably paired with at least a rod.

24. The method of claim 14, wherein securing the central region of the distractor to a midface or cranio-maxillofacial region of the facial skeleton includes attaching to the midface or cranio-maxillofacial region of the facial skeleton a distraction screw adjustably secured to the central anterior region of the distractor.

25. The method of claim 24, wherein the distraction screw is adjustably secured to a vertical rod and the vertical rod is secured to the central region of the distractor.

26. The method of claim 14, wherein the central region of the distractor includes a plurality of positions for securing the central region of the distractor to the midface or cranio-maxillofacial region of the facial skeleton.

27. The method of claim 26, wherein a threaded hole or attachment is located at each of the plurality of positions on the central region of the distractor.

28. The method of claim 14, wherein the first temporal end and the second temporal end are configured to be attached to the skull with screws.

29. The method of claim 14 wherein the second temporal end is attached to the skull at substantially eye- and temple-level.

* * * * *